United States Patent [19]

Levin et al.

[11] 4,294,931
[45] Oct. 13, 1981

[54] DEVICE FOR CONDUCTING MICROBIOLOGICAL RADIORESPIROMETRIC ASSAYS

[75] Inventors: Gilbert V. Levin, Annapolis; Patricia A. Straat, Baltimore, both of Md.

[73] Assignee: Biospherics Incorporated, Rockville, Md.

[21] Appl. No.: 107,383

[22] Filed: Dec. 26, 1979

[51] Int. Cl.³ ............................................. C12M 1/20
[52] U.S. Cl. .................................... 435/301; 206/362; 206/562; 206/563; 206/564; 220/23; 220/23.8; 422/61; 422/102
[58] Field of Search ................. 435/35, 287, 291, 296, 435/297, 298, 299, 300, 301, 807, 808; 422/61, 102; 206/562, 563, 564, 362; 220/20, 23, 23.8

[56] References Cited

U.S. PATENT DOCUMENTS

| | | | |
|---|---|---|---|
| 2,914,447 | 11/1959 | Levin | 435/35 |
| 3,386,608 | 6/1968 | Diller | 220/23.8 X |
| 3,530,917 | 9/1970 | Donovan | 220/23.8 X |
| 3,597,326 | 8/1971 | Liner | 220/23.8 X |
| 3,685,717 | 8/1972 | Seiferth et al. | 220/23.8 X |
| 3,941,660 | 3/1976 | Mirsky | 435/35 |
| 3,944,471 | 3/1976 | Waters | 435/35 |

Primary Examiner—Robert J. Warden
Attorney, Agent, or Firm—Roylance, Abrams, Berdo & Farley

[57] ABSTRACT

There is disclosed a device for conducting a microbiological radiorespirometric assay. The device comprises a support member which includes a plurality of pairs of chambers. One chamber in each pair contains a radioactive labeled substrate which is capable of being metabolized by at least some microorganisms to yield a radioactive gas. The other chamber in each pair contains a means for collecting radioactive gas. The two chambers in each pair are in communication with each other by means of a passageway, which opens into each of said chambers at the upper portion thereof. There is also disclosed a method for determining whether microorganisms contained in a sample material will metabolize a radioactive labeled substrate in the device. The method comprises placing said material in contact with a radioactive labeled substrate, collecting any gas which is evolved, exposing a photosensitive material to said collected gas and determining if a spot is produced on said photosensitive material. The production of a spot is indicative of the presence of radioactivity which indicates that the substrate has been metabolized by a microorganism.

8 Claims, 10 Drawing Figures

DEVICE FOR CONDUCTING MICROBIOLOGICAL RADIORESPIROMETRIC ASSAYS

This invention relates to a device for conducting a microbiological reaction under aerobic or anaerobic conditions. More specifically, this invention relates to a disposable plate for conducting radiorespirometric microbiological assays, such as for the detection and/or identification of microorganisms or for the determination of antibiotic susceptibility.

One of the major functions of a modern hospital or clinical laboratory is to perform microbiological analyses of blood and other patient material. This is essential in the diagnosis and treatment of numerous infectious diseases. Present costs for microbiological services are relatively high because considerable manual effort is required to make the determinations and the present technology requires that they be made in replicate portions for adequate statistical significance. Furthermore, the samples must be stored in incubators for many days, consuming valuable hospital laboratory space. Considerable attention has been focused in recent years on prospects for automating these microbial methods. The objectives are to reduce the costs, thereby making the analyses more widely available to the public, to improve the accuracy of the determinations, and to shorten the time span necessary to obtain them. The latter objectives will improve the quality of medical attention currently available.

A means has been developed for the rapid detection, identification and antibiotic sensitivity testing of microorganisms which involves radiorespirometry. Radiorespirometry is a technique for measuring the metabolic activities of living cells. Microorganisms, including bacteria, fungi, yeasts and actinomycetes, when placed in a medium containing organic substrates labeled with radioactive carbon ($^{14}C$) produce radioactive carbon dioxide ($^{14}CO_2$) as a product of substrate degradation. The $^{14}CO_2$ evolves as a gas and may be trapped and measured. The occurrence of radioactivity in the trapping agent may, therefore, be used as a positive determination of the presence of microorganisms.

Schrot, J. R., Hess, W. C., and Levin, G. V. "Method for Radiorespirometric Detection of Bacteria in Pure Culture and in Blood," *Applied Microbiology*, Vol. 26, No. 6, December, 1973; Schrot, J. R., Levin, G. V., Takeguchi, M., and Levin, R. "Radiorespirometric Identification of Bacteria," in press, both describe the high degree of sensitivity of the radiorespirometric method for microbial detection. Minute quantities of $^{14}CO_2$ gas may be easily detected. Starting from an overnight culture, radiorespirometric methods produce positive results in one-half hour, whereas conventional procedures require at least one additional day and generally longer. Conventional procedures are time-consuming, laborious and, therefore, expensive and require manipulations which can result in contamination. The radiorespirometric method has the advantage in all these areas. The method may be used for detecting bacteria in any material including blood, spinal fluid, urine, feces, hospital operating room surfaces and air, parenteral food and food processing areas, drugs, lotion, linament, cream, eyewash, cosmetics and water. Since the method is suitable for automation, large numbers of samples may be examined per day. The rapidity of the tests and the economy in materials and labor will result in considerable savings over presently available methods.

Conventional procedures for identifying bacteria involve inoculating an unknown species and monitoring the incubating tubes for one to ten days or more. The tubes are examined for gas bubbles, color changes, growth, etc. Based upon the changes observed in the media, an identification is made. The radiorespirometric method of identification, described in U.S. Pat. No. 3,969,496, is simpler in that only one signal, evolved radioactivity, is monitored as the reaction end-point. Several distinct advantages are obtained with the radiorespirometric method: (a) reactions are readable within 30 minutes to one hour; (b) results are all read in terms of radioactivity thus eliminating an error due to color interpretation; (c) a computer-generated library makes identification simple and accurate; (d) the method is simple, sterile technique is not necessary; (e) highly skilled personnel are not required since the reading and interpretation of data are done by instrument and computer; (f) bacteria, fungi, yeasts and actinomycetes can be identified by this method.

Probably the one procedure conducted in greatest volume by clinical laboratories today is antibiotic sensitivity testing. The paper disk method in which antibiotic impregnated paper disks are dropped onto an agar plate which has been seeded with the test organism is the most commonly employed method. The plate is incubated overnight and zones of inhibition around the disks indicate sensitivity. Despite its widespread use, the method is susceptible to considerable error in interpretation. An alternative method, tube dilution technique, is more accurate but is too time-consuming for most laboratories. Since the evolution of $^{14}CO_2$ from labeled medium is the result of metabolic activities of microorganisms present, any substance which inhibits the metabolism of these organisms also inhibits the $^{14}CO_2$ evolution. This is the basis of the radiorespirometric antibiotic sensitivity test. Media containing $^{14}C$ labeled substrates and various concentrations of antibiotics are inoculated with the infectious organism. Comparisons of the $^{14}CO_2$ evolved from tests with and without antibiotic concentrations provide the criteria for selecting the antibiotic and concentration effective against the organism. The generation of $^{14}CO_2$ in the trace amounts needed for detection by the radiorespirometric system significantly precedes measurable growth. Therefore, the radiorespirometric method is potentially more rapid than any other method currently available.

All of the above assay methods and research techniques involve supplying a pure or mixed culture, or substance containing such culture, with one or more compounds in which one or more of the elements is radioactive. The culture is then monitored for the evolution of radioactive gas as an index of viability, metabolic activity and/or growth. Generally, labeled carbon atoms are used in organic compounds and the gas evolved is generally radioactive carbon dioxide. However, other labels can be used in the method, such as $^{35}S$-labeled compounds which may give rise to $H_2{}^{35}S$.

One of the heretofore problems of the radiorespirometric technique is that of trapping the evolved gas and measuring its radioactivity quantitatively, accurately and rapidly. In accordance with this invention, this problem is solved by providing a device which comprises a support member which includes at least one pair of chambers. The chambers are in communication with each other by means of a passageway. The passageway opens into each of the chambers at the upper portion thereof. The device also includes a closure means for closing the chambers and the passageway.

The invention will more fully be described by reference to the accompanying drawings wherein.

Figure 1:
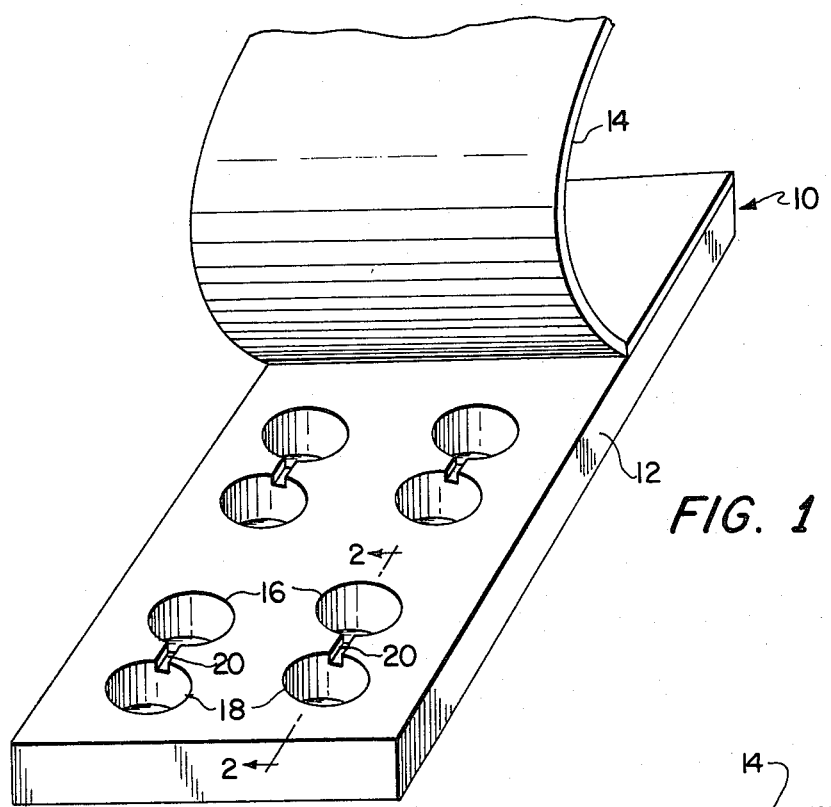
FIG. 1 is a perspective view of a microculture tray constructed in accordance with this invention.
Figure 2:
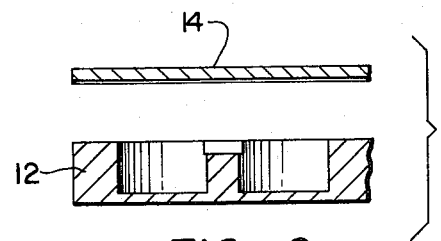
FIG. 2 is an exploded view of a cover and a sectional view of the tray shown in FIG. 1 taken along lines 2—2 of FIG. 1.

Referring more specifically to FIGS. 1 and 2, there is shown a disposable plate or microculture tray 10. The disposable plate 10 is composed of a support member 12 and a cover 14. Contained in the support member 12 are a plurality of pairs of chambers 16 and 18. Each of chambers 16 and 18 in each pair are in communication with one another by means of a passageway 20. The passageway 20 opens into each of the chambers 16 and 18 at the upper portion thereof.

Each chamber 16 is a culture well and contains liquid, dried or lyophilized growth medium. The growth medium is a radioactive labeled substrate which is capable of being metabolized so as to evolve a radioactive gas during the growth of a microorganism, e.g., a $^{14}C$ labeled substrate. Examples of such substrates include the following:

UL $^{14}C$ urea
1 $^{14}C$ lactose
15 $^{14}C$ citrate
UL $^{14}C$ ornithine
UL $^{14}C$ maltose
UL $^{14}C$ sucrose
UL $^{14}C$ D-glucose
1 $^{14}C$ DL-lysine
1 $^{14}C$ dulcitol
UL $^{14}C$ sorbitol
UL $^{14}C$ D-xylose
UL $^{14}C$ D-manitol
1 $^{14}C$ ring DL-phenylalanine
UL $^{14}C$ glycine
UL $^{14}C$ D-alanine
2 $^{14}C$ xanthine
UL L-alanine
UL $^{14}C$ formate
UL $^{14}C$ acetate
UL $^{14}C$ DL-lactate
1 $^{14}C$ fumarate
UL $^{14}C$ malate
1 $^{14}C$ gluconate
UL $^{14}C$ glutamate
UL $^{14}C$ L-tyrosine
UL $^{14}C$ L-threonine
UL $^{14}C$ L-aspartic
1 $^{14}C$ succinate
(ring 2 $^{14}C$) L-histidine
2 $^{14}C$ (ring labeled) tryptophan
1 $^{14}C$ DL-leucine
1,3 $^{14}C$ glycerol
1 $^{14}C$ D-galactose
1 $^{14}C$ D-mannose
Carbonyl $^{14}C$ DL-methionine
1 $^{14}C$ serine
1,2 $^{14}C$ oxalate
1 $^{14}C$ DL-valine
1 $^{14}C$ malonate
4 $^{14}C$ DL-asparate
(guanido $^{14}C$) DL-arginine
UL $^{14}C$ trehalose
2 $^{14}C$ uracil
UL $^{14}C$ erythritol
1,4 $^{14}C$ DL-tartrate
(carbonyl $^{14}C$) dextran
UL $^{14}C$ starch
UL $^{14}C$ cellulose
1 $^{14}C$ glucose
6 $^{14}C$ glucose
1 $^{14}C$ propionate
1 $^{14}C$ butyric The substrates should be present in the chambers 16 in sufficient amount to provide a readily detectable amount of radioactive gas upon metabolism of the microorganism. Preferably, the substrate in each chamber 16 will contain at least forty nanocuries of radioactivity.

Each chamber 18 is either a collection or counter well the bottom of which contains a getter for carbon dioxide or other gas of interest. The getter material may be something which will react with $^{14}CO_2$ (or other gas) such as hyamine hydroxide or a filter pad soaked with barium hydroxide or lithium hydroxide. Thus, if the getter material is barium hydroxide, $^{14}CO_2$ will react with it to form $Ba^{14}CO_3$. As used herein, when reference is made to collecting a gas, it is to be understood that this includes fixing the gas by means of a chemical reaction. The getter material may also contain appropriate fluors and "cocktail" materials for subsequent scintillation counting.

Figure 3:
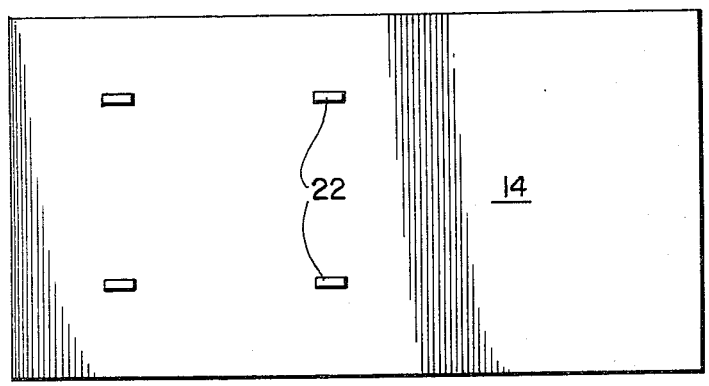
FIG. 3 is a bottom plan view of a cover which may optionally be used with the disposable tray shown in FIG. 1.
Figure 4:
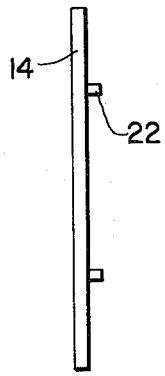
FIG. 4 is a side elevation of the cover shown in FIG. 3.

When not in use, the entire plate 10 and all of the chambers and passageways contained therein are sealed with a gas tight cover 14. The cover is secured to the support member 12 by means of adhesive or applied pressure. Optionally, as shown in FIGS. 3 and 4, the cover 14 may be provided with molded plugs 22 which may be an integral part of the cover. These plugs 22 are designed to fit into and close the passageways 20 during storage of the tray to insure that none of the getter material will migrate into the culture well during storage and that none of the radioactive material will get into the getter well during storage.

When the disposable tray 10 is to be used, the cover 14 is removed to expose the pairs of chambers 16 and 18 and passageways 20. One or more pairs of chambers may be exposed at a time. Aliquots of the material to be tested for the presence of microorganisms, or for any of the other purposes described above are added to the culture wells 16. The aliquots may be in the form of an aqueous suspension. This inoculation may be performed by introducing the suspension of microorganisms manually or by automated or mass replicating techniques. If the labeled substrate is present in dry form in the culture well 16, the aqueous medium used to introduce the microorganism into the chamber 16 reconstitutes the substrate and forms a mixture of the labeled medium and the organism.

Instead of removing the cover 14 to inoculate the culture wells 16, the cover 14 may be provided in the form of a self-sealing film and the culture material may be injected through the cover directly into the culture chamber 16.

After the culture wells 16 have been inoculated, a cover is placed over the top of the support member 12 to effect an air tight seal of each pair of chambers 16 and 18 and passageway 20. When each set of chambers 16 and 18 and the connecting passageway 20 are sealed from communication with the atmosphere, the chambers 16 and 18 are in open communication with each other via the passageway 20—i.e., following incubation, the cover with integral plugs 22 shown in FIGS. 3 and 4 would not be used. The replacement cover may be sealed to the support member by known adhesive means or by applied pressure.

Following inoculation and sealing with the cover, the plate is then incubated at the desired temperature for the desired time. During incubation, any radioactive gas evolved from the culture well 16 will migrate through the passageway 20 propelled by a concentration gradient to the counter well 18. When the desired incubation period is over, the tray is loaded into a suitable light-sensing device so that scintillation counting of each counter well 18 may be accomplished either manually or automatically. Multiple photodetectors can facilitate simultaneous counting of the samples and reduce the total elapsed time required to achieve the desired levels of statistical significance. If the getter material is applied to filter pads, the pads may also be removed from tray 10 and counted in an appropriate "cocktail" by liquid scintillation techniques.

If desired, counting of the radioactivity can also be accomplished by placing a solid state, Geiger-Mueller or other suitable radiation counting device over each counter well. Another means for determining the amount of radioactivity evolved from the culture well 16 into the counterwell 18 is by introducing a radiation-sensitive pigment or other compound into the getter film so that the film changes color or optical density in relation to the integrated dose of radioactivity received from the radioactive gas. The counter wells in such a plate can then be counted in a simple photoelectric densitometer at the end of the desired incubation period. This permits more rapid counting than can be achieved by scintillation or Geiger-Mueller counting which must accumulate events during the counting period.

The amount of radioactivity evolved from each culture well 16 into each counter well 18 may also be measured by using photographic film and radioautographic techniques to integrate the dose collected by the getter material. The radioactive gas which is evolved and collected on a filter containing getter material produces spots on the film which are then counted by a densitometer which renders counting a relatively simple and quick task compared to the necessity for counting each getter pad for approximately one minute by conventional beta detection techniques such as by the use of Geiger-Mueller tubes or liquid scintillation methods.

In using the radioautographic technique, the gettering material such as barium hydroxide in the collection well is contained on a filter pad. After the radioactivity has been collected by the getter, the getter pad is removed and then exposed to a photographic film which is sensitive to emitted beta particles. If desired, the cover plate for the disposable culture-gas collection plate may contain the film plus developer and fixer in the fashion of the Polaroid-Land technique for producing a direct positive print on the film.

A variation of the technique described in the preceding paragraph is to combine a photosensitive emulsion or material with the radioactive getter, scintillation fluors, photographic developer and hypo in the collection well, so that the photosensitive material is continuously exposed to the light photons and/or beta particles as they are evolved from the culture cell and collected in the collection cell. In this manner, the evolved radioactivity dosage would be integrated over the entire incubation period. The development of the photographic material to enhance the optical density may take place simultaneously with the exposure and collection or subsequent thereto. The use of hypo to fix the photosensitive material prior to reading its density in a densitometer is optional. This technique eliminates the necessity for expensive Geiger-Mueller or photomultiplier tubes as part of the sensing and counting mechanism and significantly reduces the elapsed time to complete the assay of the microorganisms.

If desired, after the assay has been completed, the plate may again be opened and an appropriate disinfectant added to each of the culture wells after which the cover can then be applied for final disposal. Alternatively, the plate may be heat sterilized prior to disposal. Alternative means (e.g., heat or ethylene oxide) for sterilization may be used depending upon the construction materials.

This device is for aerobic use but may also be used anaerobically by placing the device in a glove box or Brewertype jar and maintaining the atmosphere in the box or jar inert by means of gas such as nitrogen or helium. Removal of residual oxygen from this atmosphere can be accomplished by addition of pyrogallol or phosphorous pentoxide. Any device that is designed for anaerobic usage may be packaged with the nutrient under nitrogen or other inert gas and covered with a sealant such as paraffin.

The disposable plates of this invention may be constructed of any material commonly used for making items such as glass, plastic or other synthetic or natural material. The plates may be formed by any one of a number of well known molding techniques. By selection of suitable construction material, the device can also be used to monitor radioactivity released by the pyrolysis of any radioactive organic compound.

Figure 5:
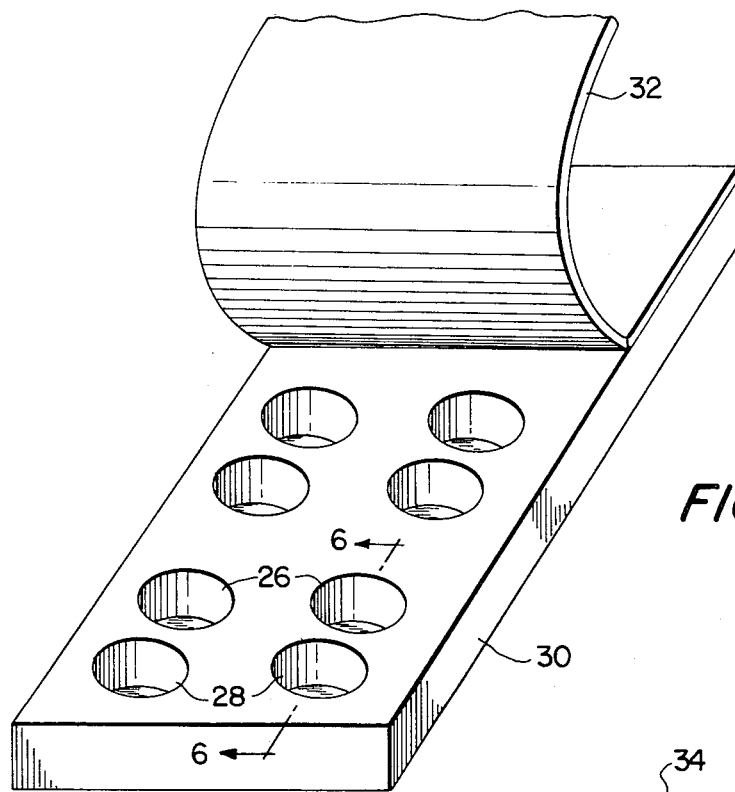
FIG. 5 is a perspective view of another embodiment of this invention.
Figure 6:
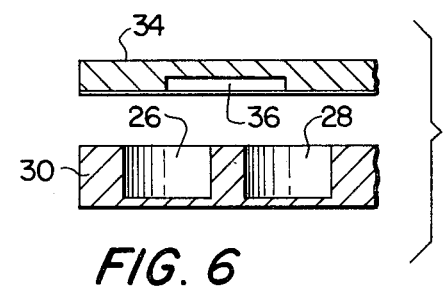
FIG. 6 is a sectional view taken along lines 6—6 of the tray in FIG. 5 and showing the tray associated with the cover used in accordance with this embodiment of the invention in an exploded view.
Figure 7:
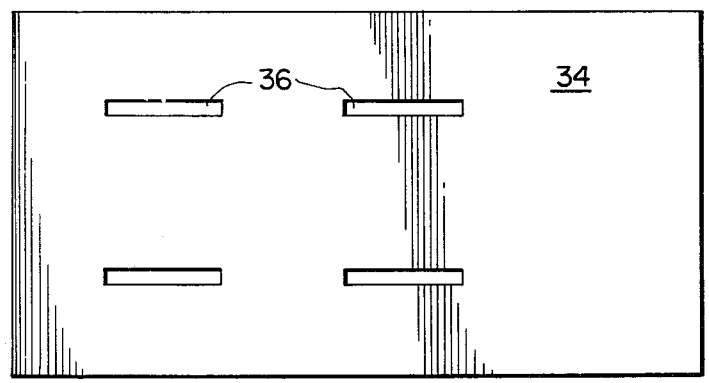
FIG. 7 is a bottom plan view of the cover shown in FIG. 6.

FIGS. 5 to 7 show another embodiment of this invention. Whereas in the embodiment shown in FIGS. 1-4, the passageway connecting the two chambers is located in the support member, in the embodiment shown in FIGS. 5-7, there is no passageway connecting chambers 26 and 28 in the support member 30. During storage, the adhesive cover 32 overlying the entire culture plate seals the culture medium and the gas collection material in their respective wells. When the plate is to be inoculated, the cover 32 is removed and discarded. After inoculation, a new disposable cover plate 34 is placed over the support member 30 and sealed by self-sealing techniques or by other sealing methods. The new cover plate 34 has a number of indentations or passageways 36 on the bottom side thereof so that when the cover 34 is placed over the support member 30, a passageway 36 overlies and connects a pair of chambers 26 and 28. Thus, the cover plate 34 provides an individual head space for each pair set of culture and collection wells 26 and 28. Gas which is evolved from the culture cell 26 will diffuse to and be absorbed by the collecting material in the corresponding collection well 28. The seal around the paired collection and culture wells 26 and 28 prevents cross-contamination of adjacent collecting cells. This embodiment eliminates the need for plugs 22 to prevent gas or liquid leakage between the paired culture and collection cells during storage of the plate as described with respect to FIGS. 3 and 4.

Figure 8:
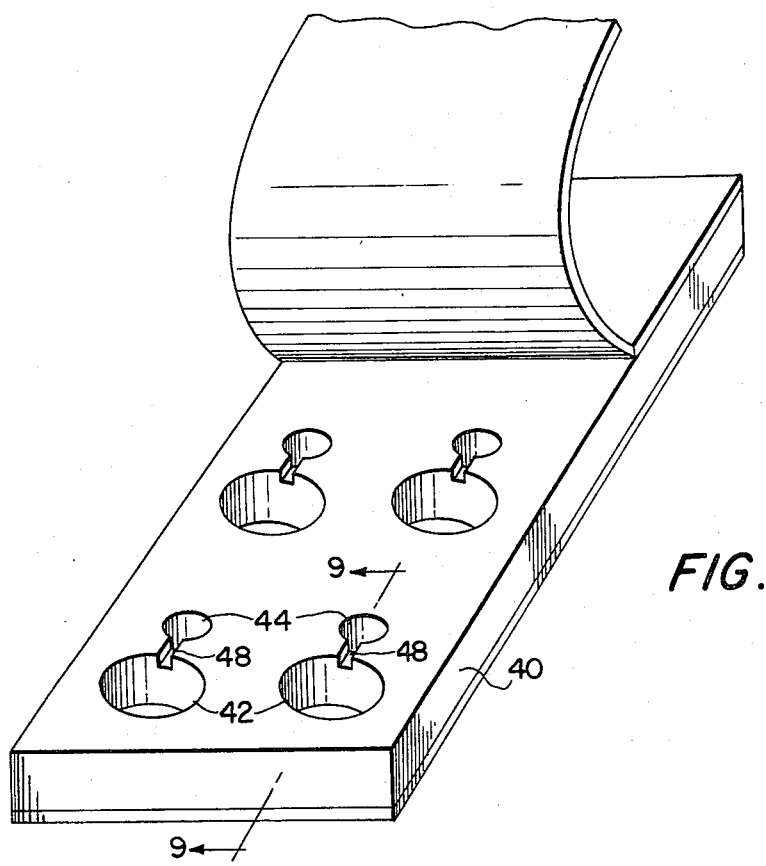
FIG. 8 is a perspective view of another embodiment of a microculture tray constructed in accordance with this invention.
Figure 9:
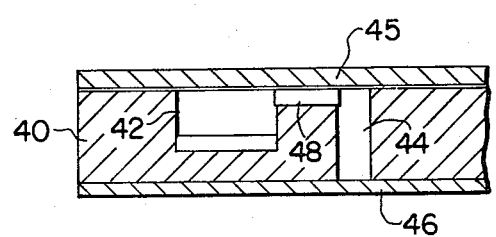
FIG. 9 is a sectional view taken along lines 9—9 of FIG. 8 and shown in conjunction with a cover.

Another preferred embodiment of this invention is illustrated in FIGS. 8 and 9. This embodiment is particularly useful when relatively low levels of radioactive gas are likely to be evolved from the culture well and when the method for quantitating gas evolution involves the use of photographic film.

Some cultures of microorganisms when incubated in the culture well produce levels of radiation as low as approximately 100 cpm as monitored by counting getter pads in either Geiger counters or liquid scintillation counters. Such low levels of radiation, particularly from $^{14}C$, are generally not detectable when photosensitive films are used to record the radiation unless exposed for a number of hours, e.g., 10 or more. Such long periods of exposure are not desired, i.e., it is desirable to identify the microorganism in less than an hour. This problem has been overcome by the embodiment of the invention shown in FIGS. 8 and 9. In accordance with this embodiment of the invention, instead of the collection well and culture well being the same size as shown in FIGS. 1 and 5, the surface area of the collection well is made much smaller than the surface area of the culture well.

As shown in FIGS. 8 and 9, there is provided a support member 40 containing a plurality of culture wells 42, collection wells 44 and cover 45. The bottom of all collection wells 44 is formed by a filter pad 46 which is soaked with getter material such as barium hydroxide. In the embodiment shown, the collection wells extend all the way through the support member and the filter pad forms the bottom of the disposable tray. However, it will be appreciated that the collection wells need not extend all the way through the support member, i.e., they may only extend to the same depth as the culture wells and getter material may simply then be placed in the bottom of the collection well. A passageway 48 connects each culture well 42 and collection well 44. While the passageways 48 are shown in FIGS. 8 and 9 located in the support member, it will be appreciated that they can also be located in the cover as previously described with respect to FIGS. 5 and 6. A cover is provided to effect an air tight seal of each set of culture well, collection well and passageway.

The wide, shallow culture well 42 induces complete and rapid gas evolution following inoculation and during incubation. However, the getter area is much smaller than the cross-sectional area of the culture well. In a typical example, the diameter of the culture well 42 is 10 mm., the diameter of the collection or getter well 44 is 3 mm., and 0.02 ml. of reaction mixture is present in the culture well. Since the area varies directly with the diameter square, the getter area is only about 10% as large as the cross-sectional area of the culture well. Thus, the gas generated from the culture well is now concentrated and the radioactivity is amplified by being collected onto a relatively small area. While the total radioactivity collected by the getter has not changed, the radioactivity per unit area of the getter pad has been significantly increased, i.e., about 10 fold.

Figure 10:
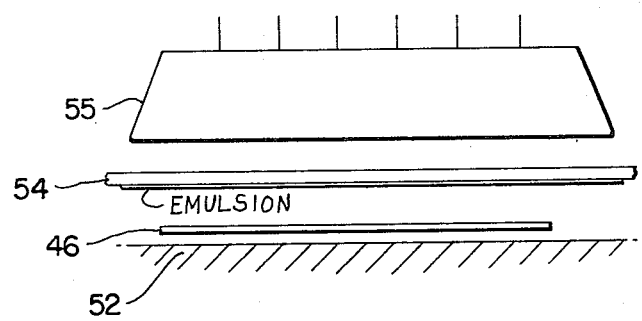
FIG. 10 is an exploded view of a film developing system.

After a suitable period of incubation, the filter pad 46 is removed from the bottom of the disposable tray. Assuming that X number of microbiological assays have been conducted using X number of culture wells and collection wells, there will be X number of circular areas of radioactivity collected on the filter pad. Photographic film, Kodak Film No. 2485 having an ASA rating of 2000, is exposed to the filter pad in the manner illustrated in FIG. 10. Thus, the filter pad 46 is placed on a support 52 with the radioactive spots facing upward. The photographic film 54 is placed emulsion side down in contact with the filter pad. A weight 55 is then placed on top of the back side of the film. As little as 30 minutes exposure produces satisfactory spots on the film that can be quantitatively measured at evolved radioactivity levels as low as 100 cpm (1000 dpm) as monitored by radioactive gas being evolved from the culture well. The preferred working range is 500–25,000 cpm.

In accordance with the practice of this embodiment of the invention, it may be necessary to adjust various factors depending upon the circumstances. For example, the time of exposure of the film to the getter pad can be changed since optical density is directly proportional to exposure time within the limits of the film. For Kodak Film No. 2485, the maximum optical density is 2.0. Films other than Kodak Film No. 2485 can be used by adjusting the exposure time proportionately to the difference in ASA ratings between the two films. To estimate the exposure time of an alternative film to produce results comparable to those described, the following relationship can be used:

$(ASA)_1(t)_1 = (ASA)_2(t)_2$ where $ASA_1$ is 2,000 (the ASA of Kodak Film No. 2485), $t_1$ is 30 minutes, $ASA_2$ is the ASA of the alternate film and $t_2$ is the exposure time for the alternate.

The diameter of the getter area can be adjusted to change the concentration of collected radioactive gas per unit area, and hence, the amplification factor. In adjusting this diameter, the following relationship holds:

$(d^2)_1(cpm)_1 = (d^2)_2(cpm)_2$

Solving for $(d^2)_1$, the equation becomes:

$(d^2)_1 = (cpm)_2/(cpm)_1(d^2)_2$ where $(d^2)_1$ is the square of the diameter of the current getter area (i.e., $3^2 = 9$), $(d^2)_2$ is the square of the diameter of the alternate getter area, $(cpm)_1$ is the cpm that with $d_1$ would produce a given O.D. (optical density), and $cpm_2/cpm_1$ is the O.D. amplification factor that would result from changing the diameter from $d_1$ to $d_2$. Substitutions are then made for $(d^2)_1$ and the amplification factor and the equation solved for $d^1_2$.

Factors to be considered in adjusting the reaction mixture to accommodate an appropriate evolution of $^{14}CO_2$ are the specific radioactive substrate, the radioactive concentration of the substrate in the reaction mixture and the yield of the reaction (i.e., moles of $^{14}CO_2$ evolved per mole substrate per unit time. Other considerations related to the reaction mixture involve the incubation time and dimensions of the reaction chamber. The volume of the reaction mixture must be sufficiently large to insure uniform mixing of all ingredients. A typical volume is 0.02 ml. The dimensions of the culture well should be such as to permit a relatively large surface area to ensure rapid diffusion of evolved gas to the getter. The amount of gas collected can be changed by changing the time of or the temperature of the reaction incubation.

It is claimed:

1. A device for conducting a microbological radiorespirometric assay under aerobic or anaerobic conditions which device comprises a support member which includes a plurality of pairs of chambers, one chamber in each said pair containing a radioactive labeled substrate which is capable of being metabolized by at least some microorganisms to yield a radioactive gas, the other chamber in each said pair containing a means for collecting radioactive gas, the two chambers in each pair being in communication with each other by means of a passageway, said passageway opening into each of said chambers at the upper portion thereof, and closure means for closing said chambers and said passageway, said passageway being situated in said support member or in said closure means.

2. A device as defined in claim 1, wherein said passageway is in said support member.

3. A device as defined in claim 1, wherein the transverse cross-sectional area of said chambers in said pairs containing a means for collecting radioactive gas is substantially less than the transverse cross-sectional area of the other chamber in said pairs.

4. A device as defined in claim 1, wherein said radioactive labeled substrate is a $^{14}C$ labeled substrate.

5. A device as defined in claim 1, wherein said means for collecting radioactive gas comprises $Ba(OH)_2$.

6. A device as defined in claim 1, wherein said radioactive labeled substrate may be degraded chemically (e.g., by pyrolysis) or biologically by being metabolized by at least some microorganisms.

7. A device for conducting a microbiological reaction under aerobic or anaerobic conditions which device comprises a support member which includes at least one pair of chambers, said chambers being in communication with each other by means of a passageway, said passageway opening into each of said chambers at the upper portion thereof, and closure means for closing and sealing said chambers and said passageway, said passageway being in said closure means.

8. A device for conducting a microbiological radiorespirometric assay under aerobic or anaerobic conditions which device comprises a support member which includes a plurality of pairs of chambers, one chamber in each said pair containing a radioactive labeled substrate which is capable of being metabolized by at least some microorganisms to yield a radioactive gas, the other chamber in each said pair containing a means for collecting radioactive gas, the two chambers in each pair being in communication with each other by means of a passageway, said passageway opening into each of said chambers at the upper portion thereof, and closure means for closing said chambers and said passageway, said passageway being in said closure means.

* * * * *